United States Patent
Johnson et al.

(10) Patent No.: US 8,114,120 B2
(45) Date of Patent: Feb. 14, 2012

(54) SYSTEM AND METHOD FOR ACTUATING A LAPAROSCOPIC SURGICAL INSTRUMENT

(75) Inventors: Gary M. Johnson, Mission Viejo, CA (US); Russell E. Ahlberg, Rancho Santa Margarita, CA (US); David Okihisa, Irvine, CA (US); Gregory I. Bak-Boychuck, Laguna Niguel, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 12/547,219

(22) Filed: Aug. 25, 2009

(65) Prior Publication Data
US 2009/0318954 A1 Dec. 24, 2009

Related U.S. Application Data

(63) Continuation of application No. 11/059,806, filed on Feb. 17, 2005, now Pat. No. 7,578,832.

(60) Provisional application No. 60/548,747, filed on Feb. 27, 2004.

(51) Int. Cl.
*A61B 17/28* (2006.01)

(52) U.S. Cl. ........................ 606/205; 606/174

(58) Field of Classification Search ............... 606/174, 606/205, 207
See application file for complete search history.

(56) References Cited

U.S. PATENT DOCUMENTS

| | | | |
|---|---|---|---|
| 5,176,699 A | 1/1993 | Markham | |
| 5,219,357 A | 6/1993 | Honkanen et al. | |
| 5,275,615 A * | 1/1994 | Rose | 606/208 |
| 5,281,220 A | 1/1994 | Blake, III | |
| 5,383,888 A | 1/1995 | Zvenyatsky et al. | |
| 5,496,317 A | 3/1996 | Goble et al. | |
| 5,496,347 A | 3/1996 | Hashiguchi et al. | |
| 5,607,450 A | 3/1997 | Zvenyatsky et al. | |
| 5,626,609 A | 5/1997 | Zvenyatsky et al. | |
| 5,700,276 A | 12/1997 | Benecke et al. | |
| 5,728,113 A | 3/1998 | Sherts | |
| 5,810,879 A | 9/1998 | de Guillebon | |
| 5,849,022 A | 12/1998 | Sakashita et al. | |
| 5,893,874 A * | 4/1999 | Bourque et al. | 606/205 |

(Continued)

FOREIGN PATENT DOCUMENTS

DE 200 01 492 6/2000
(Continued)

OTHER PUBLICATIONS

Co-Pending U.S. Appl. No. 10/976,505, filed Oct. 29, 2004. Title: Multiple-Angle Scissor Blade.

(Continued)

*Primary Examiner* — Ryan Severson
(74) *Attorney, Agent, or Firm* — John F. Heal

(57) ABSTRACT

A surgical instrument can include tips and an actuation rod having a pin and slot design where the driving slots are moved from the tips to the actuation rod in one aspect of the invention. As a result, the back end of each blade or tip can be dramatically reduced in area so that during full deflection, very little or no part of the blade or tip extends beyond the outside diameter of the shaft. In addition, the depth of each slot can be varied such that during actuation, increased tension can be put on the blades or tips throughout the cut.

14 Claims, 15 Drawing Sheets

U.S. PATENT DOCUMENTS

| | | | |
|---|---|---|---|
| 6,007,561 A | | 12/1999 | Bouorque et al. |
| 6,228,083 B1 * | | 5/2001 | Lands et al. ............ 606/50 |
| 2002/0143358 A1 * | | 10/2002 | Domingo et al. ......... 606/190 |

FOREIGN PATENT DOCUMENTS

| | | |
|---|---|---|
| DE | 201 21 161 | 4/2002 |
| DE | 203 09 774 | 10/2003 |
| EP | 0 537 574 A2 | 4/1993 |

OTHER PUBLICATIONS

Co-Pending U.S. Appl. No. 11/735,798, filed Apr. 16, 2007. Title: Laparoscopic Scissor Blade.

Co-Pending U.S. Appl. No. 11/345,964, filed Feb. 2, 2006. Title: Surgical Instrument With Removable Shaft Apparatus and Method.

Co-Pending U.S. Appl. No. 11/334,027, filed Jan. 18, 2006. Title: Disposable Laparoscopic Instrument.

International Search Report and Written Opinion of the International Searching Authority for PCT application No. PCt/US2005/005105, mailing date Aug. 23, 2005.

European Patent Office, European Search Report dated Dec. 17, 2008, for European Patent Application No. EP 08 17 0110.

"Invitation to Pay Additional Fees", International Application No. PCT/US2005/005105, and communication relating to the "Results of the Partial International Search".

* cited by examiner

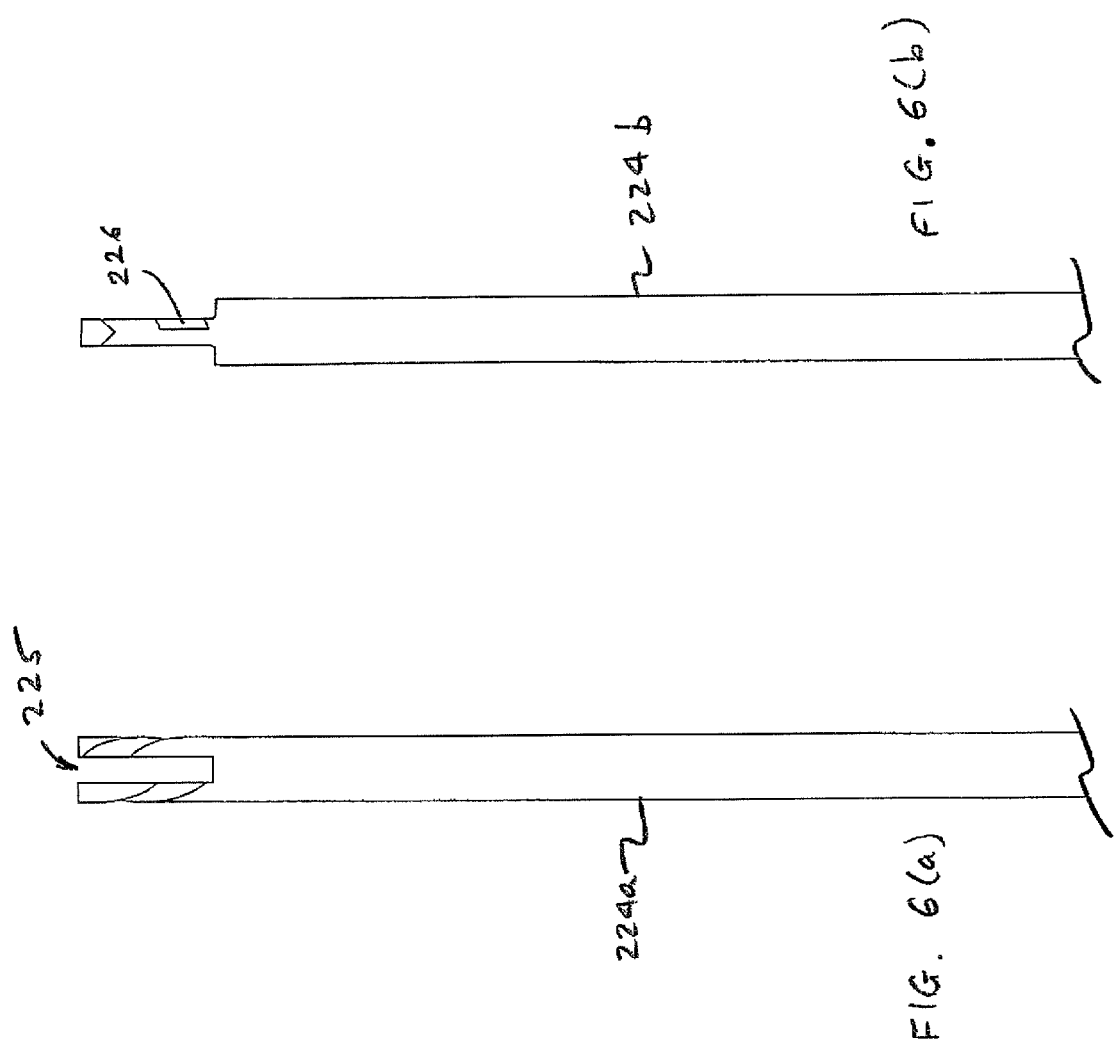

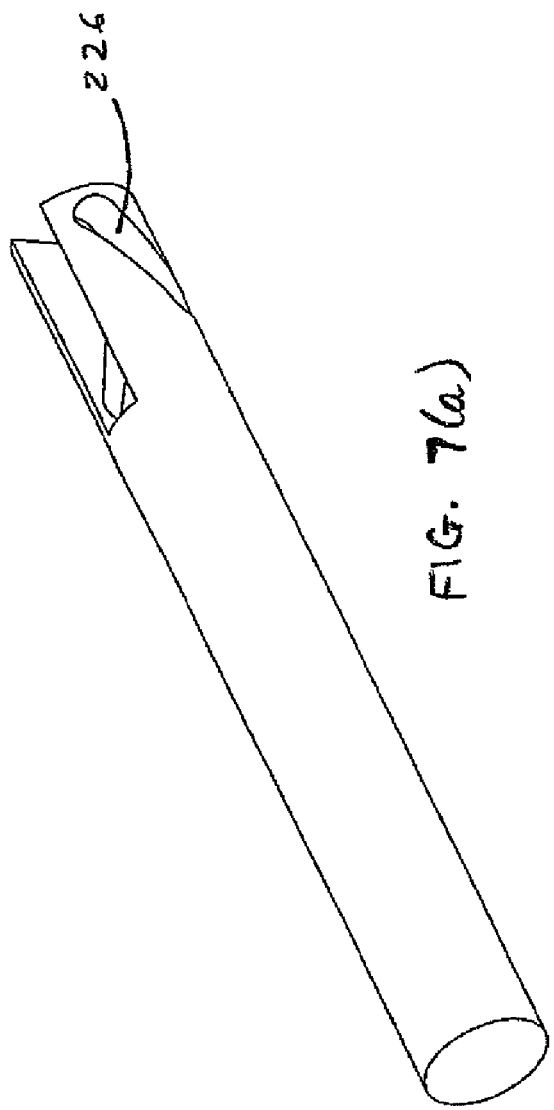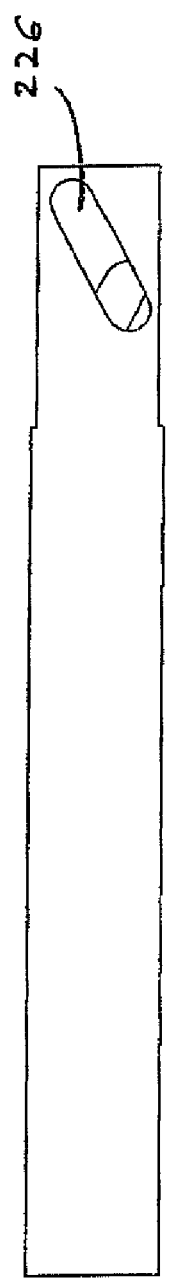
FIG. 7(a)
FIG. 7(b)

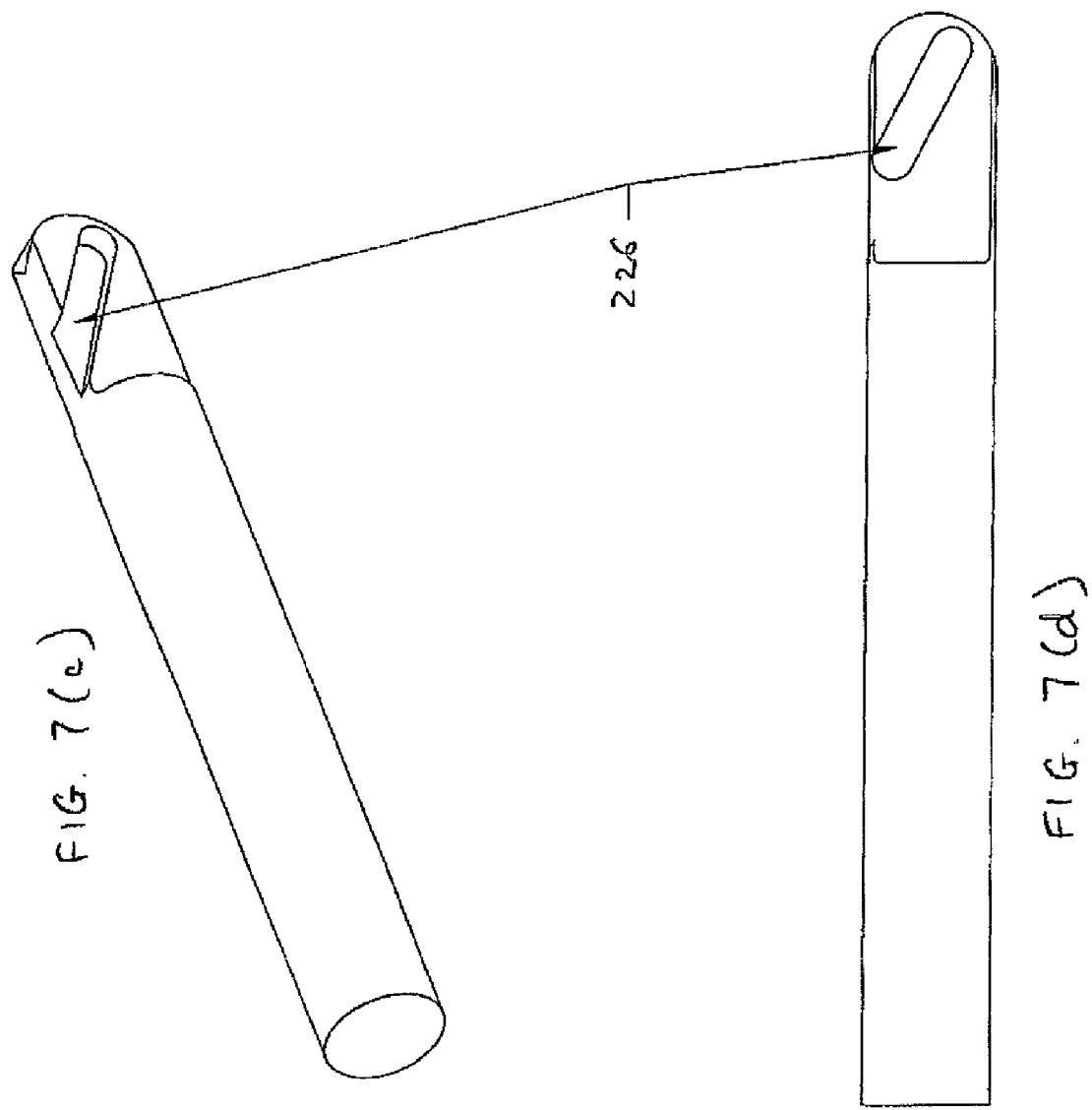

SECTION A-A

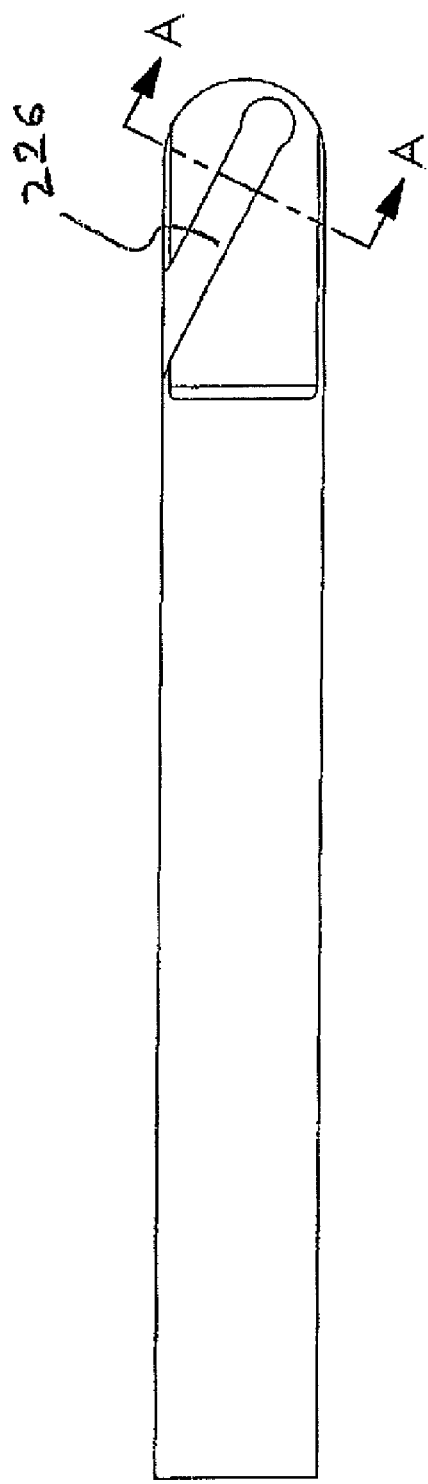
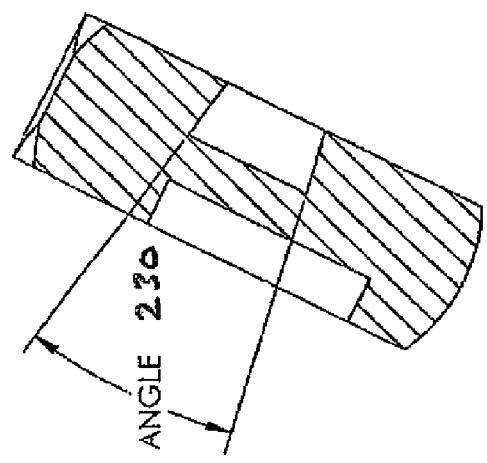
FIG. 8(d)

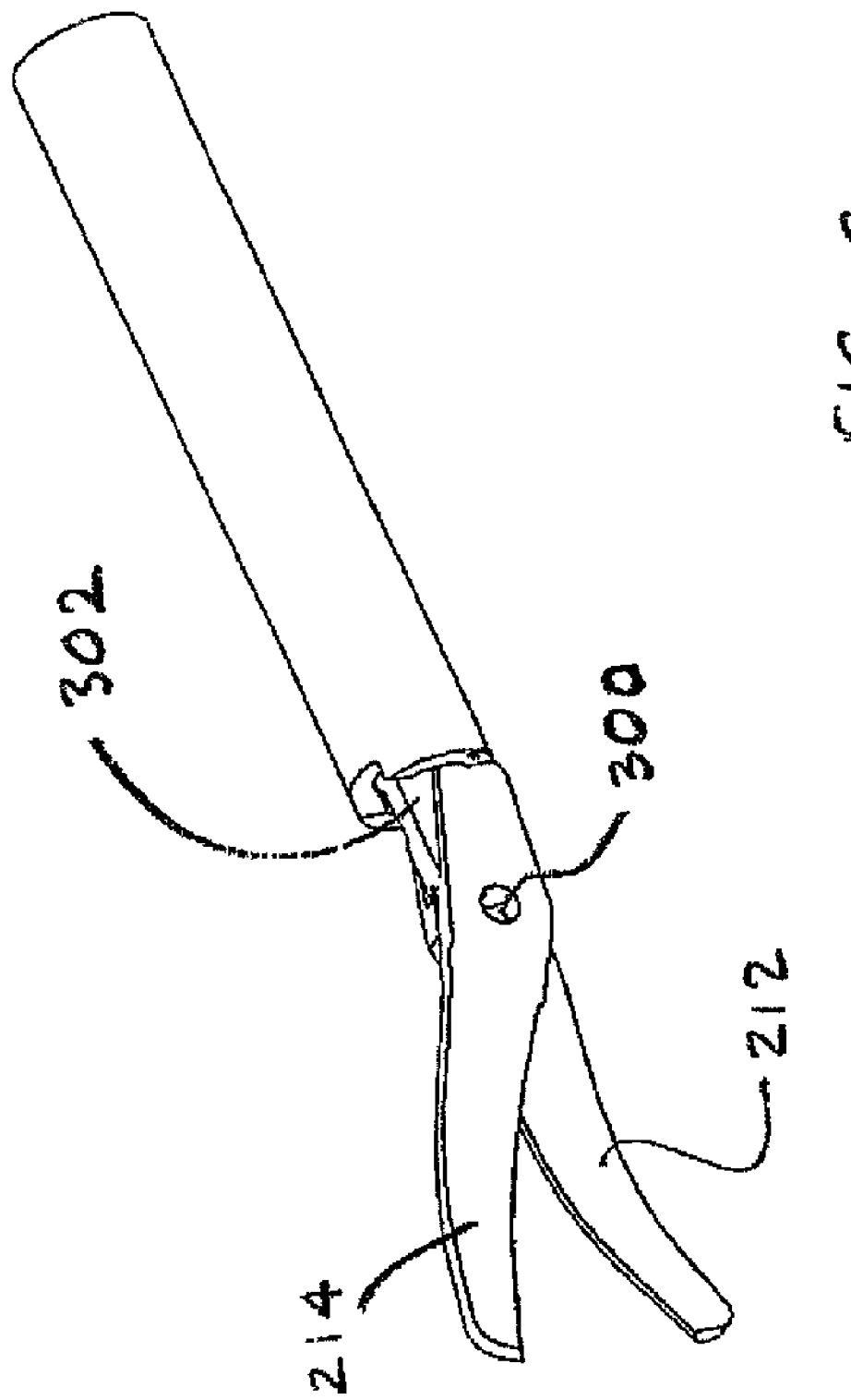

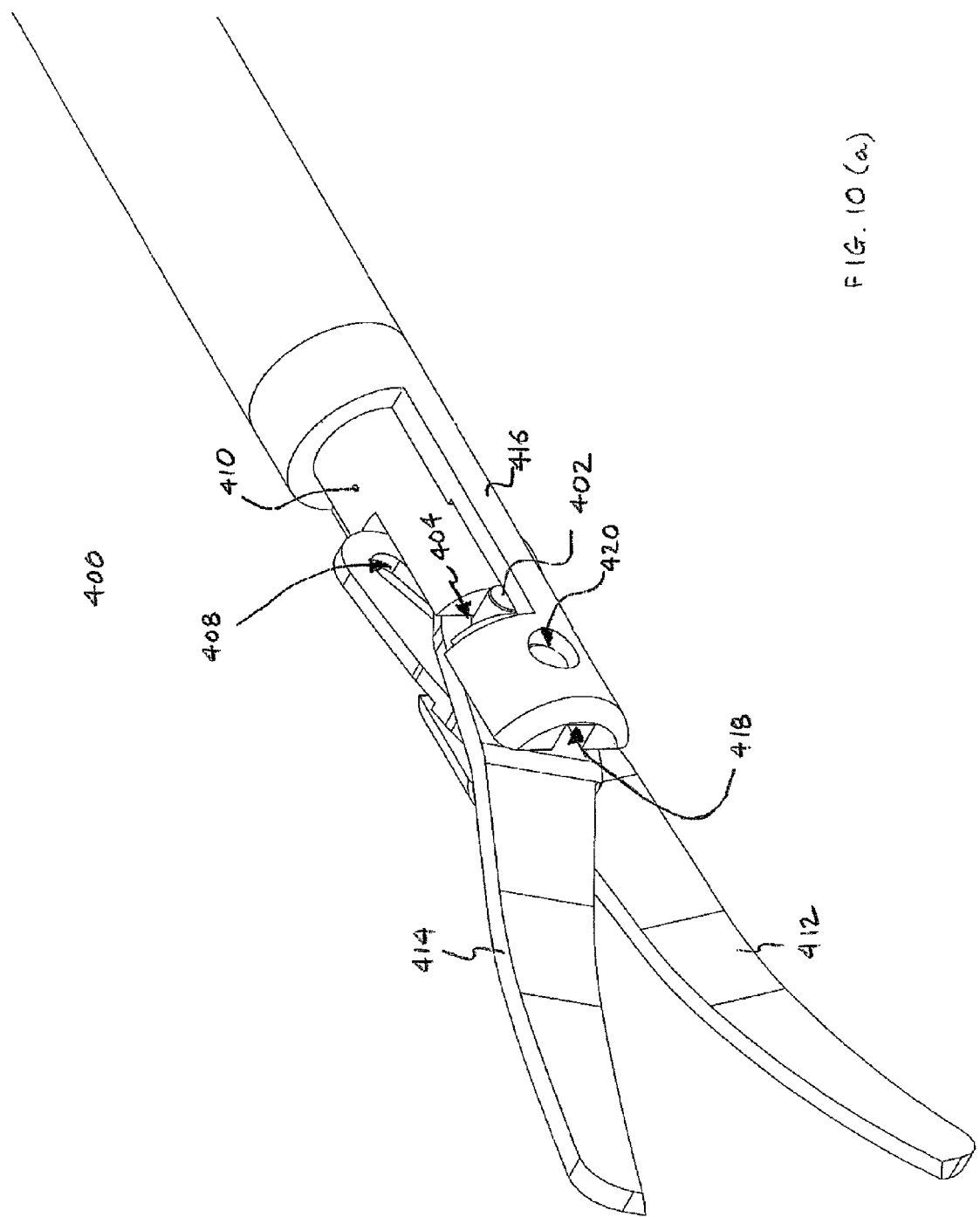

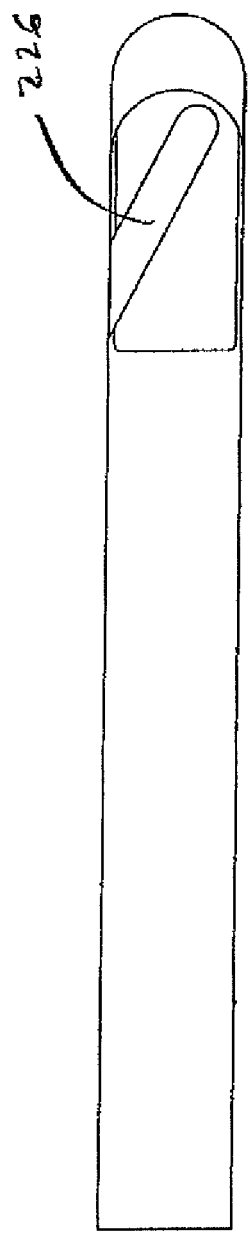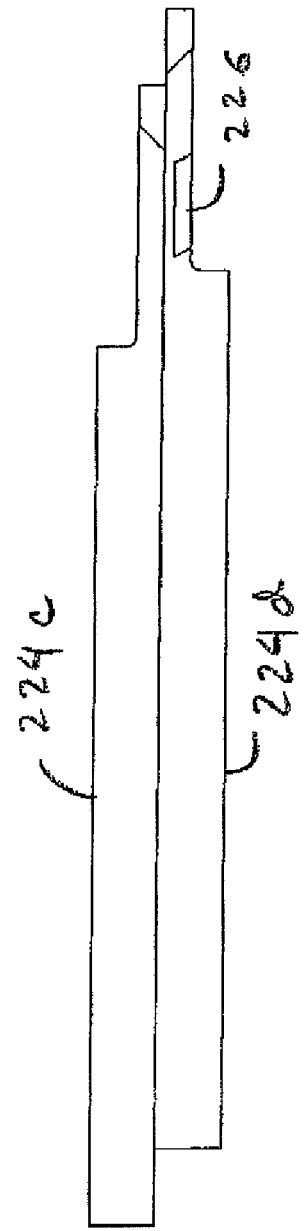
FIG. 11

SYSTEM AND METHOD FOR ACTUATING A LAPAROSCOPIC SURGICAL INSTRUMENT

This application is a continuation of U.S. patent application Ser. No. 11/059,806, entitled "SYSTEM AND METHOD FOR ACTUATING A LAPAROSCOPIC SURGICAL INSTRUMENT," filed on Feb. 17, 2005 now U.S. Pat. No. 7,578,832, issued as U.S. Pat. No. 7,578,832, which is a non-provisional application claiming the priority of provisional application Ser. No. 60/548,747, filed on Feb. 27, 2004, entitled "SYSTEM AND METHOD OF ACTUATING A LAPAROSCOPIC SURGICAL INSTRUMENT," both of which are fully incorporated herein by reference.

BACKGROUND OF THE INVENTION

1. Field of the Invention

This invention generally relates to laparoscopic surgical instruments and, in particular, to a system and method for actuating the tips of a laparoscopic surgical instrument.

2. Description of Prior Art

Laparoscopic surgical instruments or devices that use actuating blades or tips are typically activated by some mechanical means. In most cases, the surgical instruments or devices use an actuation rod to translate motion from a handle at one end to a tip at the opposite end of the device. Common to laparoscopic scissors and graspers is an actuation rod that includes a pin that works in conjunction with a slot in the tips. Moving the actuation rod cams the pin in the slot which opens and closes the tips.

The blades or tips typically have slots proximal to the pivot and because of this configuration, the back end of the blades or tips need to be quite large. When used on a grasper and the tips are in their open position, the back end of the tips extend out beyond the outside diameter of the grasper shaft and look like "wings." This may be a problem for the user and, in particular, the patient as they can catch or interfere on tissue or other devices during use.

When used on scissors, these wings will most likely be covered up with a plastic shrink tubing to insulate all the metal components during electro-surgical cautery. However, when the blades or tips are open, the wings can stretch and deform the shrink tubing. This can be problematic in that when the scissors is withdrawn from the trocar, the deformed tubing may not relax and it may catch on the end of the cannula, thereby pulling the trocar out of the patient. Accordingly, there is a need in the art for an improved system and method for actuating the blades or tips of laparoscopic instruments so as to minimize the adverse wing effect.

SUMMARY OF THE INVENTION

The invention is directed to a pin and slot design where the driving slots are moved from the blades or tips to the actuation rod in one aspect of the invention. As a result, the back end of each blade or tip can be dramatically reduced in area so that during full deflection, very little or no part of the blade or tip extends beyond the outside diameter of the outer tube or shaft. This ensures that nothing catches on the blades or tips during grasper use and the shrink tubing found on the scissors would not be deformed. This can be done because the area for the slots is not needed. Moreover, the usable area for the drive slots on the blade or tip of the actuation rod is maximized to the overall diameter of the outer tube or shaft which provides additional leverage to the blades or tips. In addition, the depth of the slot can be varied such that increased tension can be placed on the blades or tips during actuation.

More specifically, the invention is directed to a surgical instrument comprising an elongate tube extending along an axis including an actuation rod coaxially slidable within the elongate tube, a first tip including a first pin formed on a proximal end surface of the first tip, and a second tip including a second pin formed on a proximal end surface of the second tip, the second tip pivotally connected to the first tip at a common pivot pin operably connected to the elongate tube to open and close the tips in response to movement of the actuation rod. With this aspect, the actuation rod has a slot to accept the pins of the first and second tips, the slot has camming surfaces for the pins to slide within the slot, and the proximal ends of the tips extend minimally outside the diameter of the elongate tube during actuation of the tips. In another aspect, the proximal ends of the tips do not extend outside the diameter of the elongate tube during actuation of the tips. The actuation rod can be formed by machining, stamping, overmolding, casting, or metal injection molding. The pins can be formed on the proximal end surfaces of the tips by press fitting, threading, welding or bonding. The actuation rod can be a tongue actuation rod or a fork actuation rod. With the fork actuation rod, the rod can include a through slot on each side of the rod, which may be curved and transverse to one another. The tongue actuation rod can also include two curved and transverse slots on opposing sides of the tongue. It is appreciated that the slots can be open-ended or closed-ended. As stated above, the slot may have a depth that varies along the length of the slot. In particular, the different depth of the slot provides different tension along the tip. In another aspect, the tongue actuation rod includes means for ratcheting the tips into a desired position; the ratcheting means may include a series of detents.

In another aspect of the invention, there is disclosed a surgical instrument comprising an elongate tube extending along an axis including an actuation rod coaxially operable within the elongate tube, a first tip including a first cam slot with a first camming surface, and a second tip including a second cam slot with a second camming surface, the second tip pivotally connected to the first tip at a common pivot pin operably connected to the elongate tube to open and close the tips in response to movement of the actuation rod. With this aspect, the actuation rod includes a third slot to hold a floating drive pin, the floating drive pin is placed through the first and second cam slots, and the proximal ends of the tips extend minimally outside the diameter of the elongate tube during actuation of the tips. In another aspect, the proximal ends of the tips do not extend outside the diameter of the elongate tube during actuation of the tips. The third slot may be a vertical slot and the elongate tube may further comprise a floating drive pin slot at the proximal portion of the tube.

In yet another aspect of the invention, there is disclosed a surgical instrument comprising a shaft assembly extending along an axis including a rotatable outer shaft and a coaxial inner rod, a first tip including a first pin formed on a proximal end surface of the first tip, and a second tip including a second pin formed on a proximal end surface of the second tip, the second tip pivotally connected to the first tip at a common pivot pin operably connected to the shaft assembly to open and close the tips in response to movement of the outer shaft. With this aspect, the outer shaft has a slot to accept the pins of the first and second tips, the slot has camming surfaces for the pins to slide within the slot, and the proximal ends of the tips extend minimally outside the diameter of the shaft assembly during actuation of the tips, which are actuated by rotating the outer shaft. In another aspect, the proximal ends of the tips do not extend outside the diameter of the elongate tube during actuation of the tips.

These and other features and advantages of the invention will become more apparent with a discussion of the embodiments in reference to the associated drawings.

DESCRIPTION OF THE DRAWINGS

FIGS. 6(a) and 6(b) illustrate a fork actuation rod and a tongue actuation rod of the invention, respectively;

FIGS. 7(a) and 7(b) illustrate a perspective view and a side view of the fork actuation rod having slots on both sides of the fork end;

FIGS. 7(c) and 7(d) illustrate a perspective view and a side view of an actuation rod having a slot with an open end in accordance with another aspect of the invention;

FIG. 8(d) illustrates a slot in an actuation rod having a locking mechanism in accordance with another aspect of the invention;

FIG. 9 illustrates a perspective view of an assembled surgical instrument having a fixed tip and a mobile tip in accordance with another aspect of the invention;

FIGS. 10(a) and 10(b) illustrate perspective views of a surgical instrument having an actuation rod with a vertical slot to hold a floating drive pin in accordance with another aspect of the invention;

FIG. 11 illustrates an actuation rod that is split into at least two pieces to provide independent motion to the tips in accordance with another aspect of the invention.

DESCRIPTION OF THE INVENTION

Figure 1:
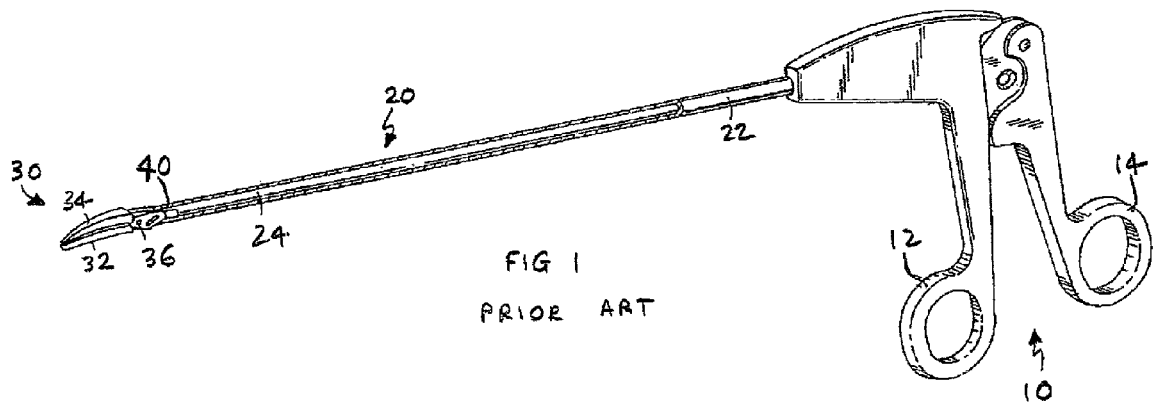
FIG. 1 illustrates a perspective view of a laparoscopic view of a surgical instrument of the prior art.

Referring to FIG. 1, there is shown a perspective view of a laparoscopic surgical instrument 100 of the prior art as shown in U.S. Pat. No. 5,626,609, which is incorporated herein by reference. The surgical instrument 100 typically comprises a handle assembly 10 having a fixed handle 12 and a pivoting handle 14. Extending from the handle assembly 10 is a shaft assembly 20 comprising an outer tube 22 and an inner actuation rod 24. The actuation rod 24 slides in the outer tube 20 in a coaxial relationship. The outer tube 22 may be secured to the fixed handle 12, while the actuation rod 24 may be secured to the pivoting handle 14. Attached at a distal end of the shaft assembly 20 is a tool mechanism 30, which comprises of a lower jaw 32 and an upper jaw 34. The tool mechanism 30 is connected to the shaft assembly 20 at pivot point 36 through linkage mechanism 40. During use, as the actuation rod 24 slides within the outer tube 22, the linkage mechanism 40 is actuated to pivot jaws 32 and 34 about pivot point 36 to open and close the jaws.

Figure 2:
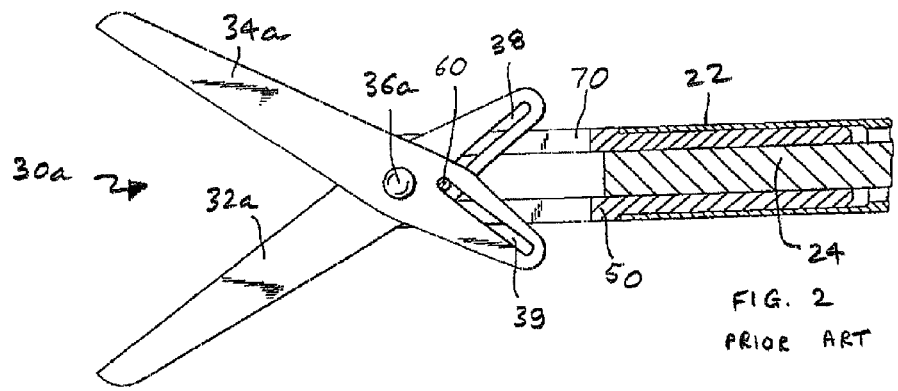
FIG. 2 illustrates a side cutaway view of a tool mechanism of the surgical instrument of FIG. 1 in the open position.
Figure 3:
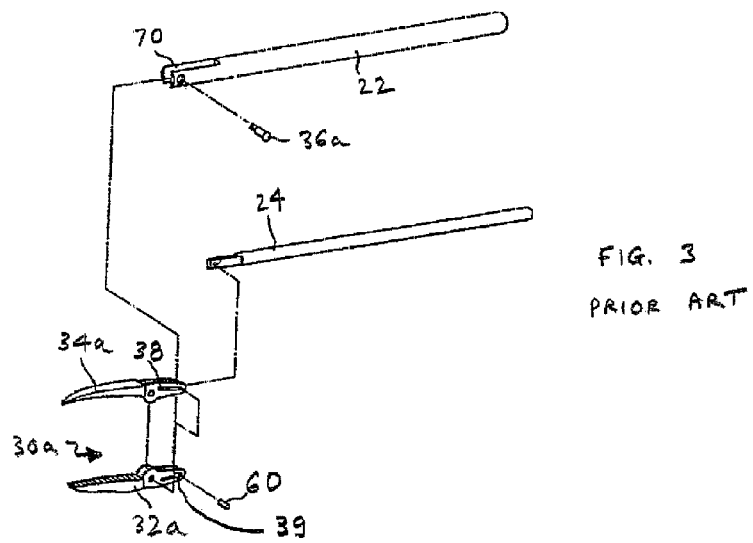
FIG. 3 is an exploded perspective view of FIG. 2.

Referring to FIGS. 2 and 3, there is shown a tool mechanism 30a of the prior art which includes, for example, a first scissor blade 32a and a second scissor blade 34a. In this embodiment, a housing member 50 is attached to the outer tube 22, and the tool mechanism 30a is attached to the housing member 50. As the handles move, the actuation rod 24 slides through the outer tube 22 towards the tool mechanism 30a. As illustrated in FIG. 2, scissor blades 32a, 34a are provided with cam slots 38 and 39, respectively, which slots accept a bearing post 60 which is attached to inner rod 24. As the rod 24 moves, the bearing post 60 slides within cam slots 38, 39 to pivot blades 32a, 34a about pivot pin 36a to open and close the blades. A drawback of this tool mechanism 30a is when the blades 32a, 34a are open, the tail end of the blades pass through slot 70 in housing member 50 to allow the blades to open. That is, the tail end of the blades 32a, 34a extend out beyond the outside diameter of the surgical instrument and look like "wings." This may be a problem for the user as they can catch or interfere on tissue or other devices during use. Moreover, when the blades 32a, 34a are open, the wings can stretch and deform the plastic shrink tubing that is used to insulate the shaft assembly 20. For example, this can be problematic in that when the instrument is withdrawn from a trocar after a procedure, the deformed tubing may not relax and it may catch on the end of the cannula, thereby pulling the trocar out of the patient.

Referring to FIGS. 4(a)-4(c), there is shown a surgical instrument 200 in accordance with a first aspect of the invention having a tool mechanism 210 including a first blade or tip 212 and a second blade or tip 214, each of which has a pin 218 and 216, respectively, formed at the proximal end. The pins 218, 216 are fixed, typically by welding, to blades or tips 212, 214 and extend outwardly of the surface of the back end of the blades or tips 212, 214. The blades or tips 212, 214 are overlapped in a scissors configuration and are held in a pivotal relationship with an outer tube by a common pin 220. A novel feature of the invention is it includes the tool mechanism 210 that interacts with a slotted actuation rod 224 as further explained below. It is appreciated that because the blades or tips 212, 214 include pins 218, 216, rather than slots, much area is not needed on the back ends. This is beneficial because the "wingspan" of the blades or tips 212, 214 when opened is minimized if not eliminated. In addition, the overall strength of the blades or tips 212, 214 and the rod 224 is maximized because both the rod and the blades are integral or are single piece components.

The fork actuation rod 224 can be formed in a number of different ways. For example, the desired features can be machined from a solid rod or tube of a desired diameter. In another aspect, a strip of metal can be stamped with the desired slots at the end, then the tube can be rolled into a particular diameter where the slotted end can form a "fork". In yet another aspect, the fork features at the end of the actuation rod can be overmolded onto a shaft to provide a cost effective component.

As to the tongue actuation rod, it can be formed in a similar way to the fork actuation rod. More specifically, machining the detail in the tip is an option as is overmolding the detail. The end of the actuation rod can also be formed as a separate part, i.e., molded, machined, cast, MIM, etc., with the feature detail in it and then attached to a standard length shaft by means of a thread, snap, adhesive, welding process or some other attachment method.

Figure 4:
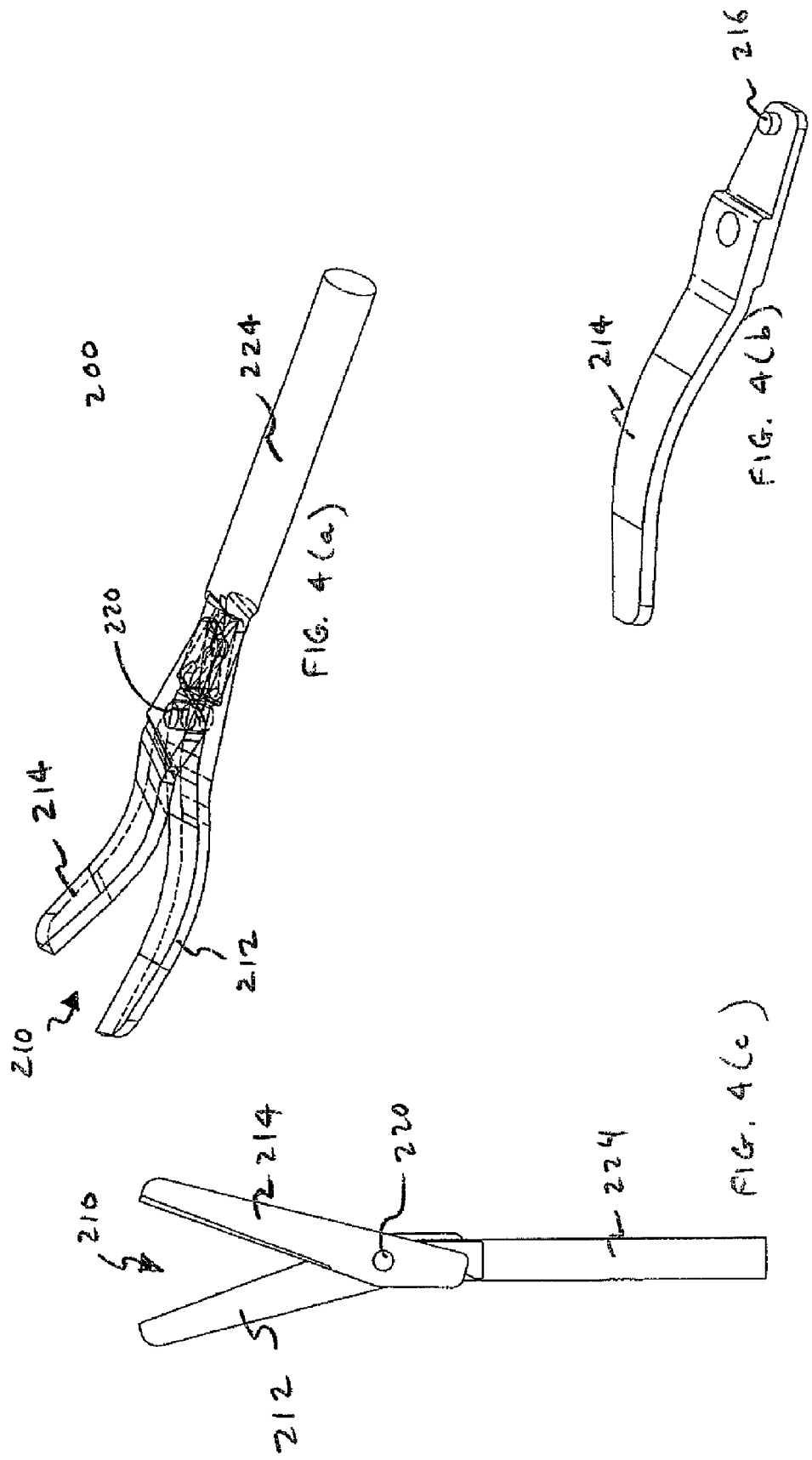
FIGS. 4(a)-4(c) illustrate a perspective view of a laparoscopic surgical instrument of the invention, a perspective view of a blade or tip of the tool mechanism of the invention, and a side view of FIG. 4(a), respectively.
Figure 5:
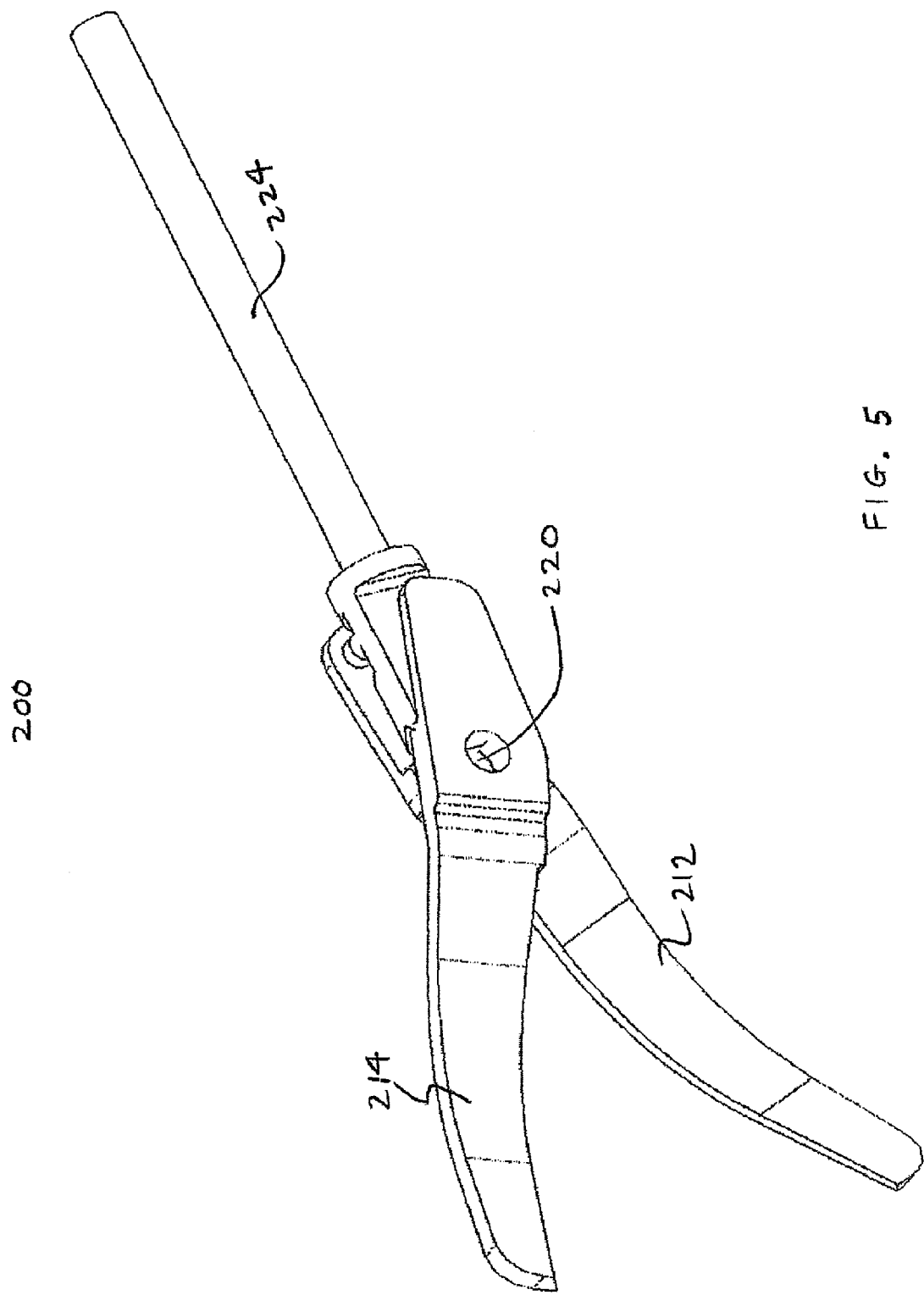
FIG. 5 illustrates a perspective view of an assembled surgical instrument of the invention having mobile tips and an actuation rod.

Referring to FIG. 5, there is shown a perspective view of the tool mechanism 210 of FIG. 4 being connected to the actuation rod 224. It is appreciated that there are numerous methods of manufacturing the blades or tips 212, 214. For example, the blades or tips 212, 214 can be formed from conventional stamping and then heat treated. In another example, the blades or tips 212, 214 can be formed from a blank of pre-hardened material and then EDM cut, waterjet cut, laser cut or even machined to obtain the final shape. It should be noted that pins 218, 216 in the back ends of the blades or tips 212, 214 can be formed directly onto the blades or pins themselves, or they can be added after the pins have been manufactured.

The pins 218, 216 can be locked in any one or a combination of the following ways: press-fitted, swaged, threaded and/or welded. To manufacture the pin as part of the blades or tips 212, 214, a multitude of processes can be used. A sheet of material can be machined to include a pivot hole as well as the pin. The sheet can then be heat treated and sent to a form grinder, which can grind one profile of the blade or tip. The ground plate can then be sent to be EDM cut and the second profile can be cut out. This type of process can yield numbers components, with the drive pin integrally located, with relatively low cost.

There are also additional processes that can yield the entire part from a minimum number of operations. These can include but are not limited to metal injection molding (MIM), casting, and powder metallurgy (PM). The final blade can also then be sent to be sharpened or other post processing.

The following is a discussion of the pin and slot design of the invention, where there are a number of advantages which can be realized. For example, (1) The back end of each blade or tip is reduced in area so that during full deflection, very little or no part of the blade or tip extends beyond the outside diameter of the outer tube or shaft. This ensures that nothing catches on the blades or tips during grasper use and the shrink tubing found on scissors would not be deformed. This can be done because the area for the slots is not needed;

(2) The usable area for the drive slots on the blade or tip of the actuation rod is maximized to the overall diameter of the outer tube or shaft which provides additional leverage to the blades or tips; and (3) If channels are used on the actuation rod, the depth of the channels can be varied such that increased tension can be placed on the blades during actuation.

Moreover, by moving the slot from the blades or tips to the actuation rod, the "wingspan" of the blades can be reduced or eliminated because the back end does not need to endcase the slot, but rather a small pin which minimizes the chance of catching on tissue, other instruments or suture.

Referring to FIGS. 6(a) and 6(b), there are shown the end of the actuation rod which can be a fork design 224a or a tongue design 224b. With the fork design 224a, a through slot 226 can be formed on each side of the rod 224a. The back end of the blades or tips can be inserted into the rod where the pin of the first blade or tip can be locked into the first slot and the pin of the second blade or tip can be locked into the opposing second slot. The blades or tips can be fixed by a common pivot point on the outer tube or shaft. When the actuation rod is moved in one direction, the blades or tips will cam via the pins and the slots 226. The pin that locks each blade or tip into the shaft can be integral to the blades or tips or they can be separate components. Similarly to the fork design 224a, the tongue design 224b can include a slot 226 on each side of the tongue as further discussed below.

Figure 7E:
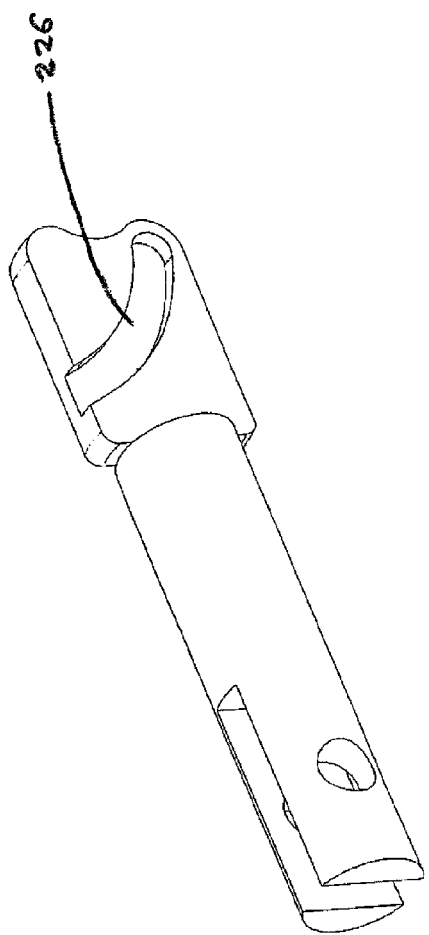
FIGS. 7(e) and 7(f) illustrate a perspective view and a side view of an actuation rod having a curved slot in accordance with another aspect of the invention.
Figure 7F:
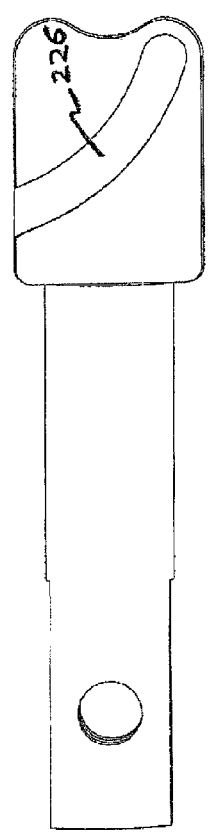

Referring to FIGS. 7(a) and 7(b), there are shown a perspective view and a side view of the actuation rod 224 incorporating slots 226 on both sides of the tongue end, respectively. As explained above, the blades or tips can have pins on the back end that nest in the slots of the rod. The rod may be pushed forward or pulled backwards to cam the blades or tips, which are pivoted by a common pivot point that is attached to the outer tube or shaft. In some cases, it is beneficial to have different slot designs to actuate the tips to different openings, at different speeds, for different length tips and for varying force. Referring to FIGS. 7(c) and 7(d), the slots 226 can include an open or closed end slot (or combination of both) as desired. FIGS. 7(e) and 7(f) illustrate an actuation rod having a curved slot in accordance with another aspect of the invention. It is appreciated that as the jaw providing the blades or tips of the invention articulates a pivot point, the distance between the pin and slot and the hinge vary depending on the actuation rod position. Accordingly, the curved slot of the invention can be used to compensate for this phenomenon and provide for a more linear relation between the actuation rod and the jaw motion. For example, the slot can be shaped to provide for more control as the blades or tips are nearing the closed position, and greater acceleration as the blades or tips are near the opened position. With this aspect, the instrument can be tuned to provide the desired instrument control and user feedback.

Figure 8A:
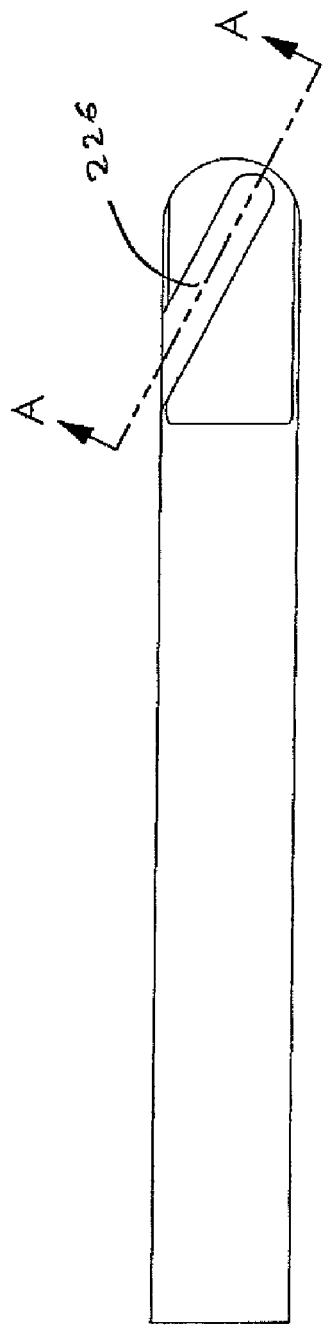
FIGS. 8(a) and 8(b) illustrate a side view and a cross-section view of an actuation rod having an angled slot in accordance with another aspect of the invention.
Figure 8B:
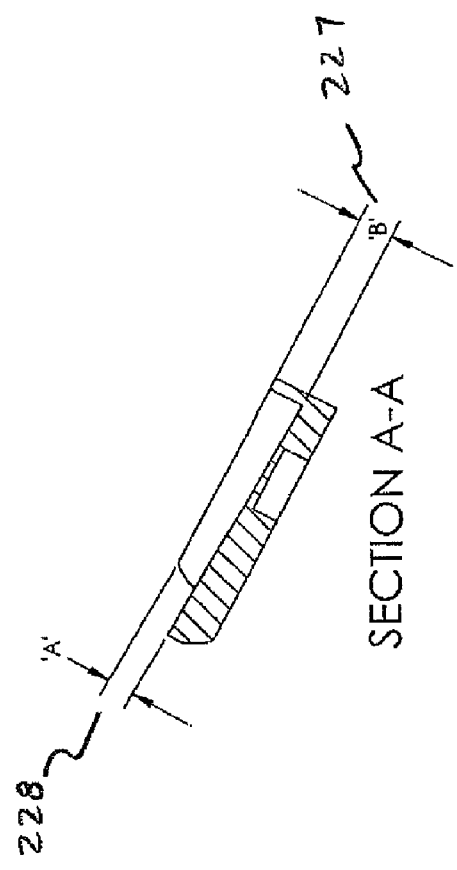

In another embodiment of the invention as illustrated in FIGS. 8(a) and 8(b), a slot 226b for the tongue can be formed such that it has an angle to it. In other words, the depth of the slot 226b at one end ('B') 227 may be deeper or shallower than at the other end ('A') 228. This is beneficial because as the actuation rod 224 is pulled, and the blades or tips close, the pins camming in the slots can be forced apart by the angle at the bottom surface of the slots. This would spread the back end of the blades or tips which in turn push the front of the blades or tips together putting more tension along the cutting surface.

Figure 8C:
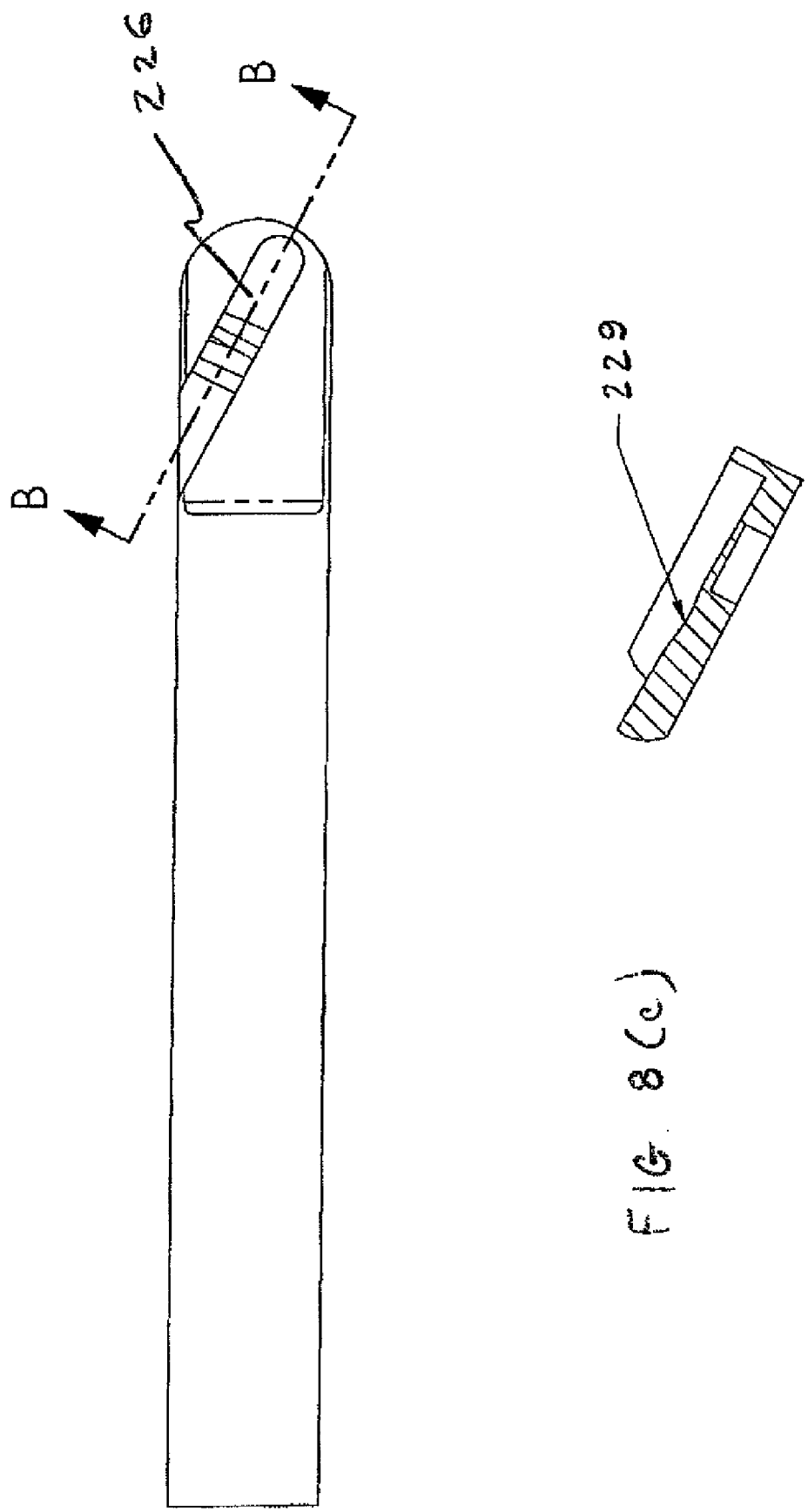
FIG. 8(c) illustrates a slot in an actuation rod having a detent or elevation shift to temporarily lock or ratchet the tips into a desired position in accordance with another aspect of the invention.

In yet another aspect of the invention as illustrated in FIG. 8(c), there is shown a slot 226c having a detent or elevation shift 229 to temporarily "lock" or "ratchet" the blade or tip into a desired position without affecting the linear motion of the jaws relative to the handle actuation. FIG. 8(d) illustrates that a slot 226d can also be formed with different cross sections, e.g., slot 226d having a locking mechanism with a dovetail profile 230. With this embodiment, the mating pin on the blades or tips can match the slot to "lock" it in.

In another aspect of the invention as illustrated in FIG. 9, both blades or tips 212, 214 do not need to be mobile. That is, one blade 212 may be fixed while the other blade 214 may actuate. The mobile blade 214 may contain a pin 300 and an actuation rod 302 that would contain only one slot to actuate the blade 214.

Figure 10B:
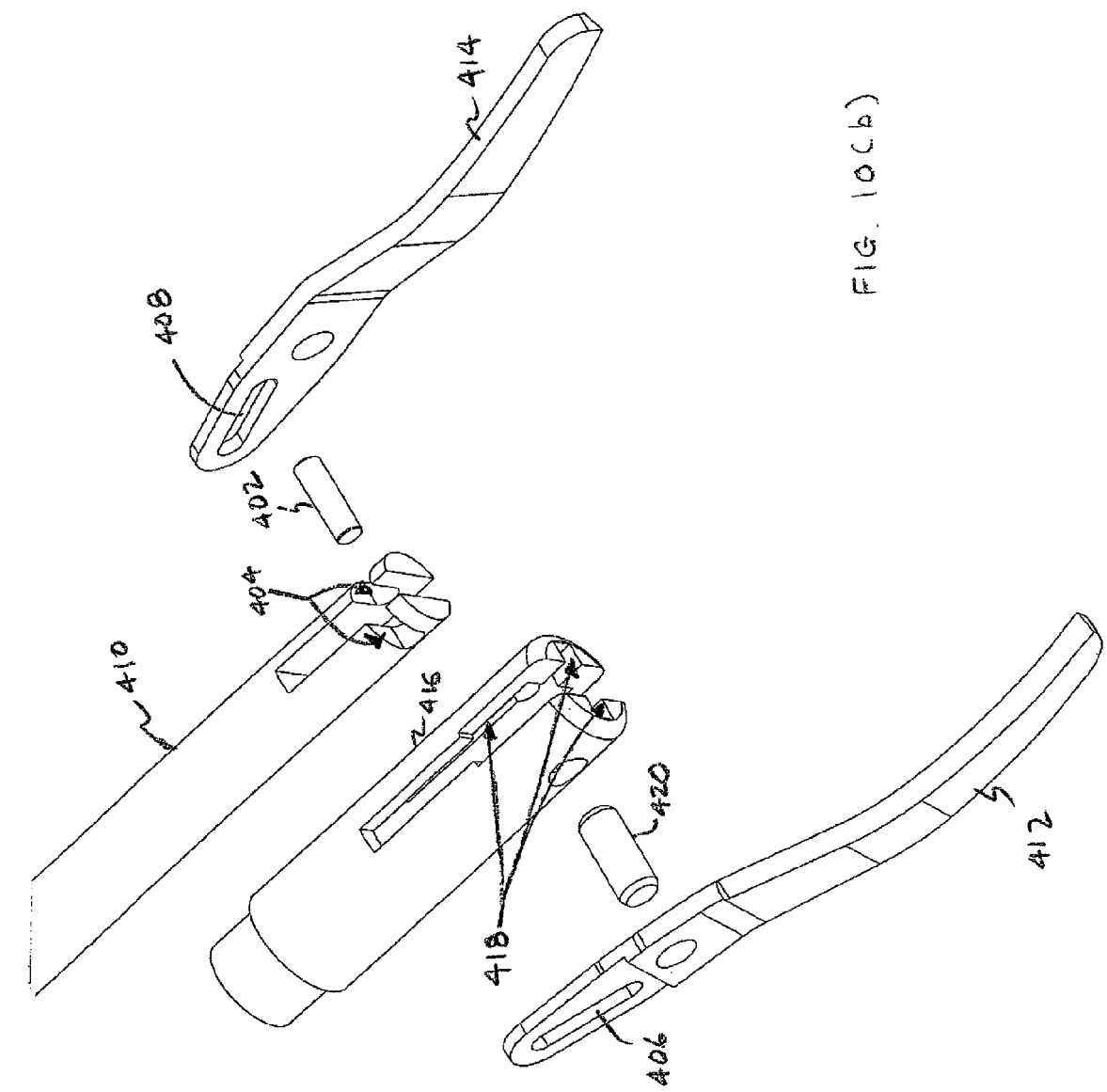

In yet another aspect of the invention, FIGS. 10(a) and 10(b) illustrate a surgical instrument 400 providing a floating drive pin 402 in an actuation rod 410. More specifically, the actuation rod 410 includes a vertical slot 404 to allow the drive pin 402 to float in. With this aspect, the drive pin 402 is positioned through slots 406, 408 of blades or tips 412, 414, respectively, and is located in the actuation rod slot. An outer shaft tip 416 has a floating pin slot 418 from the tip in. The floating drive pin 402 slides in this slot and is contained therein. A pivot pin 420 is located at the tip of the shaft to lock the tip assembly in place. Referring to FIG. 11, there is shown another aspect of the invention where the slots or channels 226 can be of any of the above-described design, however, the actuation rod is split into a plurality of multiple pieces 224c, 224d to provide independent motion to the blades or tips. This would be useful if the blades or tips need to be articulated at different speeds, or over different distances.

Figure 12:
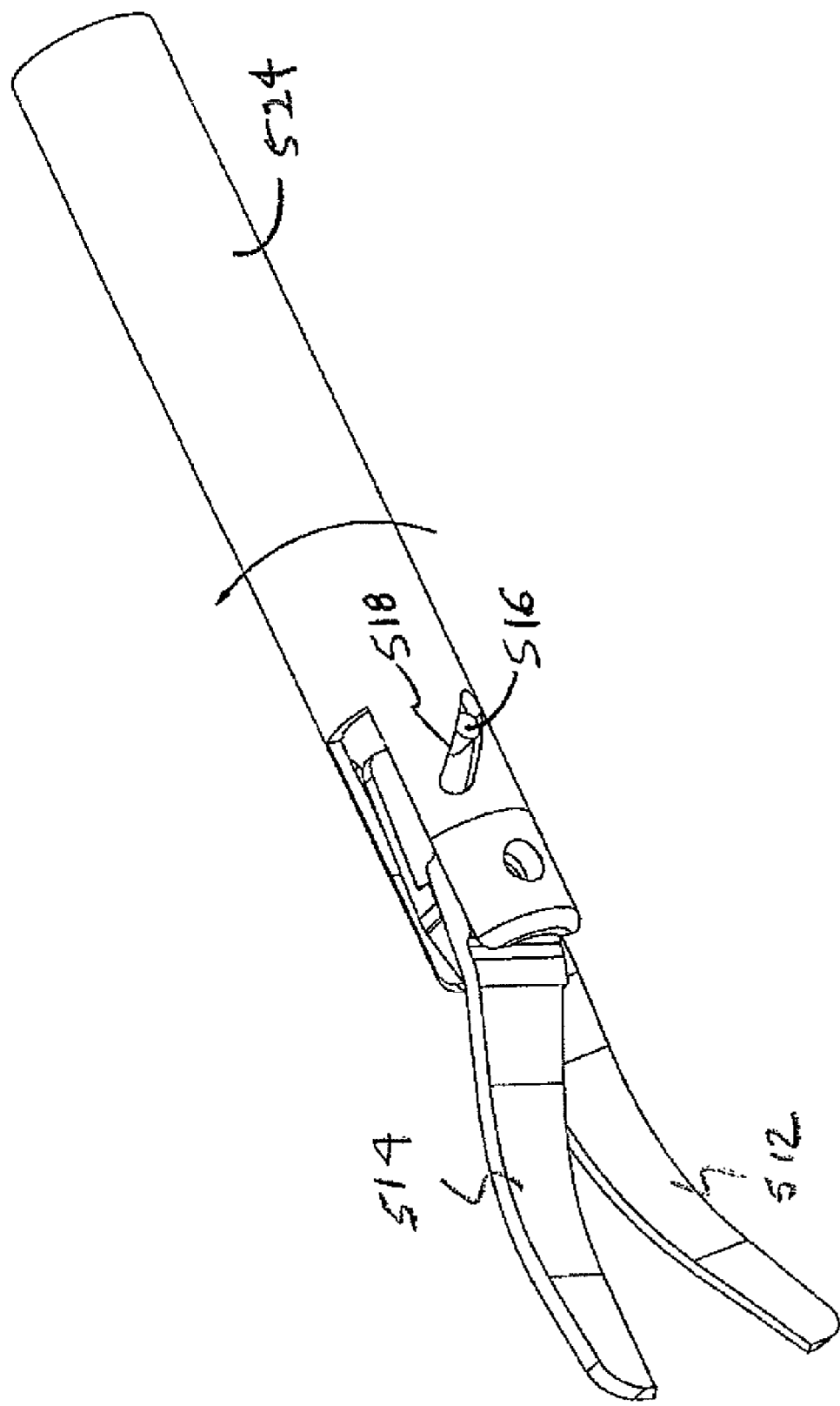
FIG. 12 illustrates an outer tube or shaft having slots to actuate the pins in the tips of a surgical instrument in accordance with another aspect of the invention.

Referring to FIG. 12, there is shown another aspect of the invention where the slot or channel is located in an outer shaft 524 rather in the actuation rod. In particular, the blades or tips 512, 514 are similar to those of the previous design, except pin 516 of blade 512, for example, extends to the outer shaft 524, which includes slots 518 to receive pins 516, 520 of blades or tips 512, 514, respectively. With this aspect of the invention, blades or tips 512, 514 are actuated by rotating the outer shaft 524, which cause pins 516, 520 to cam along the slots 518 in the outer shaft 524 and actuate the blades 512, 514 open and closed. The outer shaft 524 can also be made up of multiple pieces and can include a channel rather than a through slot.

It will be understood that many other modifications can be made to the various disclosed embodiments without departing from the spirit and scope of the invention. For these reasons, the above description should not be construed as limiting the invention, but should be interpreted as merely exemplary of preferred embodiments.

The invention claimed is:

1. A surgical instrument, comprising:
an elongate tube extending along an axis;
an actuation rod coaxially slidable within the elongate tube;
a first tip having a proximal end with a proximal end surface, the first tip comprising a first pin formed on the proximal end surface of the first tip; and
a second tip having a proximal end with a proximal end surface, the second tip comprising a second pin formed on the proximal end surface of the second tip, the second tip being pivotally connected to the first tip at a common pivot pin operably connected to the elongate tube to open and close the tips in response to movement of the actuation rod, and
wherein the actuation rod comprises a fork actuation rod having a first side and a second side, wherein each of the first side and the second side comprises a slot to accept a corresponding one of the pins of the first and second tips, the slots each having camming surfaces for the corresponding pin to slide within the slot, and the slot of the first side extending transverse to the slot of the second side of the actuation rod, and wherein the proximal ends of the tips extend minimally outside the diameter of the elongate tube during actuation of the tips.

2. The surgical instrument of claim 1, wherein the actuation rod is formed by one of machining, stamping, overmolding, casting, and metal injection molding.

3. The surgical instrument of claim 1, wherein the slot on each side of the actuation rod comprises a through slot.

4. The surgical instrument of claim 3 wherein at least one of the slots is one of an open-end slot and a closed end slot.

5. The surgical instrument of claim 1, wherein the proximal end of the first tip and the proximal end of the second tip are positioned between the first side of the fork actuation rod and the second side of the fork actuation rod.

6. A surgical instrument comprising:
an elongate tube extending along an axis;
a tongue actuation rod coaxially slidable within the elongate tube;
a first tip having a proximal end with a proximal end surface, the first tip comprising a first pin formed on the proximal end surface of the first tip; and
a second tip having a proximal end with a proximal end surface, the second tip comprising a second pin formed on the proximal end surface of the second tip, the second tip being pivotally connected to the first tip at a common pivot pin operably connected to the elongate tube to open and close the tips in response to movement of the actuation rod, and
wherein the tongue actuation rod comprises a slot to accept the pins of the first and second tips, the slot having camming surfaces for the pins to slide within the slot and a bottom surface extending between the camming surfaces, and the slot comprising a ratchet mechanism formed in the bottom surface, the ratchet mechanism defining a locked position of the tips.

7. The surgical instrument of claim 6, wherein the ratchet mechanism comprises at least one elevation shift.

8. The surgical instrument of claim 6, wherein the tongue actuation rod comprises a first side and a second side opposite the first side, the tongue actuation rod comprising the slot formed on the first side of the tongue actuation rod, and a second slot formed on the second side of the tongue actuation rod, the second slot extending transversely to the first slot.

9. The surgical instrument of claim 6, wherein the proximal ends of the tips do not extend outside the diameter of the elongate tube during actuation of the tips.

10. The surgical instrument of claim 6, wherein the ratchet mechanism comprises at least one detent formed in the slot.

11. A surgical instrument comprising:
an elongate tube extending along an axis;
a tongue actuation rod slidable within the elongate tube along the axis, the tongue actuation rod comprising a first side surface and a second side surface opposite the first side surface;
a first tip having a distal end with a first blade formed thereon and a proximal end with a proximal end surface, the first tip comprising a first pin formed on the proximal end surface of the first tip; and
a second tip having a distal end with a second blade formed thereon, a proximal end with a proximal end surface, the second tip comprising a second pin formed on the proximal end surface of the second tip, the second tip being pivotally connected to the first tip at a common pivot pin operably connected to the elongate tube to open and close the tips in response to movement of the actuation rod such that a cutting surface is defined between the first blade and the second blade, and
wherein the tongue actuation rod comprises a first slot formed in the first side surface and a second slot formed in the second side surface to accept the corresponding first and second pins of the first and second tips, the first and second slots each having side walls defining camming surfaces for the pins to slide within the slot, and at least one of the first and second slots having a bottom surface extending between the side walls and defining a depth relative to the corresponding first and second side surfaces that varies along a length of the slot.

12. The surgical instrument of claim 11, wherein the at least one of the first and second slots having a bottom surface defining a depth that varies along the length of the slot has a first end and a second end opposite the first end, and a first depth at the first end and a second depth at the second end, the second depth different from the first depth.

13. The surgical instrument of claim 11, wherein the depth of the at least one of the first and second slots having a bottom surface defining a depth that varies along the length of the slot varies along the length of the slot to apply a tension to the cutting surface.

14. The surgical instrument of claim 13, wherein the depth of the at least one of the first and second slots having a bottom surface defining a depth that varies along the length of the slot varies such that as the first and second tips are pivoted to a closed position relative to one another, the pins are forced apart relative to the corresponding first and second side surfaces.

* * * * *